(12) United States Patent
Hommeltoft et al.

(10) Patent No.: US 8,388,903 B2
(45) Date of Patent: Mar. 5, 2013

(54) SUPPORTED IONIC LIQUID REACTOR

(75) Inventors: Sven Ivar Hommeltoft, Pleasant Hill, CA (US); Zhen Zhou, Emeryville, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 197 days.

(21) Appl. No.: 12/824,893

(22) Filed: Jun. 28, 2010

(65) Prior Publication Data

US 2011/0318233 A1 Dec. 29, 2011

(51) Int. Cl.
*B01J 8/02* (2006.01)
*B01J 10/00* (2006.01)

(52) U.S. Cl. .................... 422/211; 422/129

(58) Field of Classification Search .............. 422/129, 422/211

See application file for complete search history.

(56) References Cited

U.S. PATENT DOCUMENTS

| | | | |
|---|---|---|---|
| 3,116,346 A | 12/1963 | Van Dyke | |
| 4,011,166 A | 3/1977 | Schenach | |
| 4,990,709 A | 2/1991 | Wu | |
| 5,208,403 A | 5/1993 | Buchanan et al. | |
| 6,395,948 B1 | 5/2002 | Hope et al. | |
| 7,432,408 B2 * | 10/2008 | Timken et al. | 585/709 |
| 2002/0169071 A1 * | 11/2002 | Sauvage et al. | 502/150 |
| 2004/0035293 A1 | 2/2004 | Davis, Jr. | |
| 2005/0033102 A1 * | 2/2005 | Randolph et al. | 585/708 |
| 2006/0287521 A1 | 12/2006 | Davis, Jr. | |
| 2007/0295647 A1 | 12/2007 | Brownscombe et al. | |
| 2008/0306319 A1 * | 12/2008 | Earle et al. | 585/516 |
| 2009/0030229 A1 * | 1/2009 | Riisager et al. | 560/129 |
| 2009/0107032 A1 | 4/2009 | Lacheen et al. | |
| 2009/0170687 A1 | 7/2009 | Luo et al. | |
| 2009/0176956 A1 | 7/2009 | Grinstaff et al. | |
| 2009/0306444 A1 | 12/2009 | Elomari et al. | |
| 2010/0025292 A1 | 2/2010 | Hommeltoft et al. | |
| 2010/0065476 A1 | 3/2010 | Hommeltoft et al. | |

FOREIGN PATENT DOCUMENTS

| | | | |
|---|---|---|---|
| WO | 2005002726 | | 1/2005 |
| WO | WO2005002726 | * | 1/2005 |
| WO | 2007124397 | | 11/2007 |
| WO | WO2007124397 | * | 11/2007 |

OTHER PUBLICATIONS

Hommeltoft, Applied Catalysis A: General 221 (2001) 421-428.
J. Am. Chem. Soc. 2002, 124(44), 12932-12933; ionic liquids have been used on solid support for homogeneous hydroformylation.

* cited by examiner

*Primary Examiner* — Walter D Griffin
*Assistant Examiner* — Lessanework Seifu
(74) *Attorney, Agent, or Firm* — Susan M. Abernathy

(57) ABSTRACT

A chemical reactor, comprising:
a) an ionic liquid, supported on a porous solid; and
b) a Brønsted acid; wherein the ionic liquid serves as an adsorbent and promoter for the Brønsted acid, and the Brønsted acid is a catalyst for alkylation, oligomerization, or a combination thereof of a hydrocarbon mixture comprising at least one alkylatable hydrocarbon and at least one alkylating agent in the chemical reactor. Also, a chemical reactor, comprising:
a) a gaseous HCl, which is a catalyst for oligomerization of olefins;
b) a chloroaluminate ionic liquid, supported on a porous solid, wherein the chloroaluminate ionic liquid serves as an adsorbent and promoter for the catalyst;
and c) a volatile hydrocarbon, which evaporates to control a heat of reaction in the chemical reactor.

21 Claims, 2 Drawing Sheets

SUPPORTED IONIC LIQUID REACTOR

This application is related to two co-filed patent applications, titled "PROCESS TO CONTROL PRODUCT SELECTIVITY" and "SUPPORTED LIQUID PHASE IONIC LIQUID CATALYST PROCESS," herein incorporated in their entireties.

TECHNICAL FIELD

This application is directed to a chemical reactor comprising an ionic liquid on a solid support, and a Brønsted acid.

SUMMARY

This application provides a chemical reactor, comprising:
a) an ionic liquid, supported on a porous solid; and
b) a Brønsted acid; wherein the ionic liquid serves as an adsorbent and promoter for the Brønsted acid, and the Brønsted acid is a catalyst for alkylation, oligomerization, or a combination thereof of a hydrocarbon mixture comprising at least one alkylatable hydrocarbon and at least one alkylating agent in the chemical reactor.

This application also provides a chemical reactor, comprising:
a) a gaseous HCl, which is a catalyst for oligomerization of olefins;
b) a chloroaluminate ionic liquid, supported on a porous solid, wherein the chloroaluminate ionic liquid serves as an adsorbent and promoter for the catalyst; and
c) a volatile hydrocarbon, which evaporates to control a heat of reaction in the chemical reactor.

DETAILED DESCRIPTION

Figure 1:
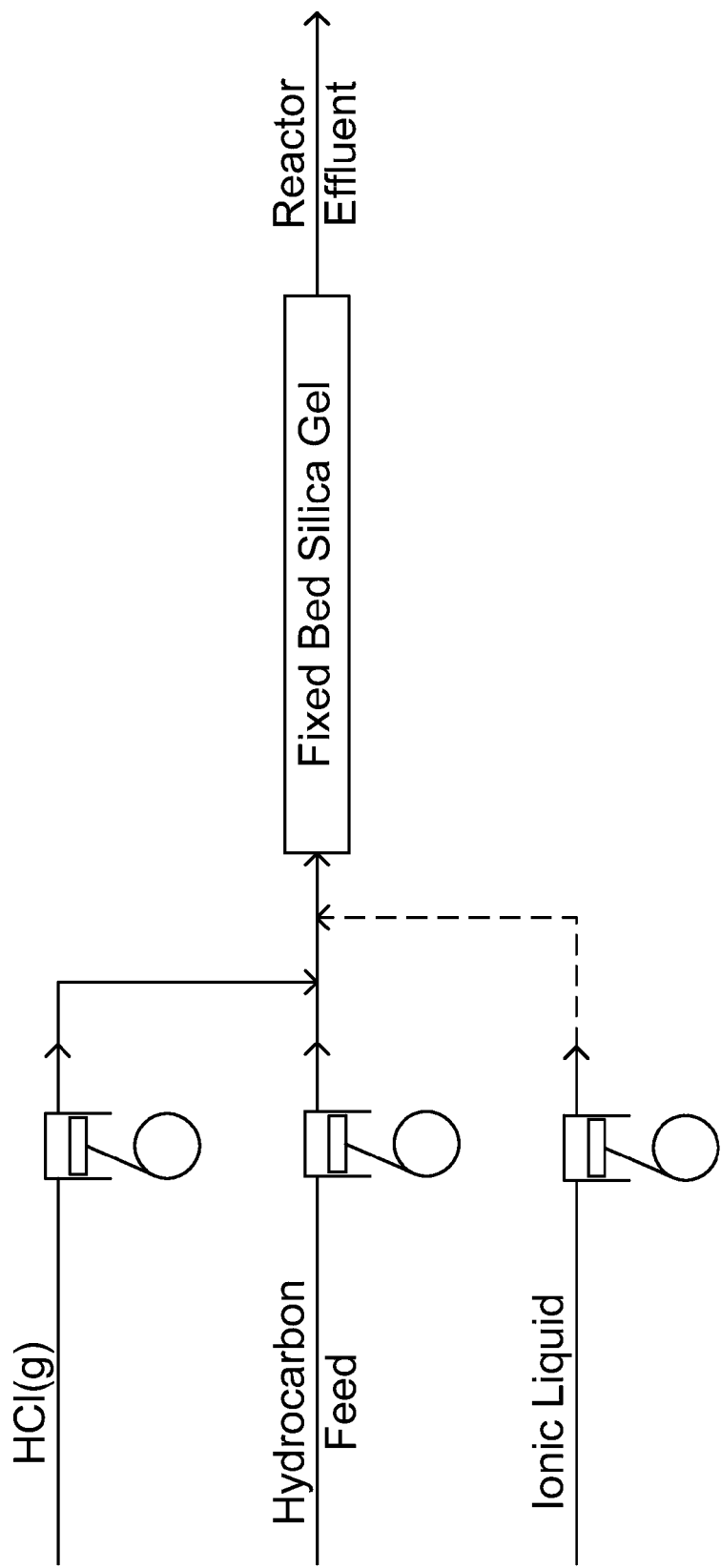
FIG. 1 is a process flow diagram of the experimental setup used for Example 1 in this disclosure.

In one embodiment, the chemical reactor produces liquid hydrocarbon products. Examples of liquid hydrocarbons that can be made in the chemical reactor are alkylate gasoline blending components, naphtha, heavy naphtha, jet fuel, diesel, base oil, and bright stock.

The porous solid supports the ionic liquid. Examples of suitable porous solids include silica, alumina, titania, zirconia, thoria, boria, niobium oxide, tin oxide, and mixtures thereof. In another embodiment, the porous solid can comprise polymer resins with pyridine groups, amine groups, or other basic groups; or porous forms of carbon, including forms of activated carbon. For example, the porous solid can be protonated forms of polyvinyl pyridine crosslinked with divinyl benzene and/or polystyrene amines In one embodiment, the porous solid is able to form an adduct with the ionic liquid and the porous solid does not react or disintegrate under operating conditions in the chemical reactor.

The porous solid, for example, can be in the shape of pellets, multi-channel cylinders, a honeycomb, a helix, and a variety of polygonal arrangements typical for fixed bed reactors. In one embodiment, the porous solid is a porous particulate. A porous particulate can have pores up to 200 Å, such as in the range of 20 to 150 Å, or 30 to 100 Å. In another embodiment, the porous solid comprises a particulate having a diameter in the longest direction from 25 to 3000 μm.

In one embodiment, the porous solid is placed in a fixed bed and a pore volume in the reactor is greater than 25 vol % of a total volume of the reactor. In other embodiments the pore volume is from greater than 25 vol % up to 70 vol %, from 30 to 50 vol %, from 35 to 45 vol %, or approximately 40 vol % of the total volume of the reactor.

The ionic liquid is composed of at least two components which form a complex. The ionic liquid comprises a first component and a second component. The first component of the acidic ionic liquid can comprise a Lewis Acid. The Lewis acid can be a metal halide compound selected from components such as Lewis Acidic compounds of Group 13 metals, including aluminum halides, alkyl aluminum halide, gallium halide, and alkyl gallium halide. Other Lewis Acidic compounds, such as Group 3, 4, and 5 metal halides, in addition to those of Group 13 metals, can also be used. Other specific examples include $ZrCl_4$, $HfCl_4$, $NbCl_5$, $TaCl_5$, $ScCl_3$, $YCl_3$, and mixtures thereof. The periodic table by the International Union of Pure and Applied Chemistry (IUPAC), version date 22 Jun. 2007, is used for defining the Groups 3, 4, 5, and 13 metals. In one embodiment the first component is aluminum halide or alkyl aluminum halide. For example, aluminum trichloride can be the first component of the acidic ionic liquid.

The second component making up the ionic liquid is an organic salt or mixture of salts. These salts can be characterized by the general formula Q+A−, wherein Q+ is an ammonium, phosphonium, boronium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^-$, and 3-sulfurtrioxyphenyl. In one embodiment the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl substituted pyridinium halide compounds for example 1-butylpyridinium halide, benzylpyridinium halide, or hydrocarbyl substituted imidazolium halides, such as for example, 1-ethyl-3-methyl-imidazolium chloride.

In one embodiment the ionic liquid is an acidic ionic liquid catalyst selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. For example, the acidic ionic liquid catalyst can be an acidic haloaluminate ionic liquid, such as an alkyl substituted pyridinium chloroaluminate or an alkyl substituted imidazolium chloroaluminate of the general formulas A and B, respectively.

A

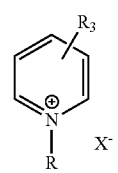

-continued

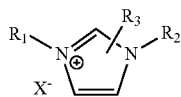

In the formulas A and B; R, $R_1$, $R_2$, and $R_3$ are H, methyl, ethyl, propyl, butyl, pentyl or hexyl group, X is a chloroaluminate. In the formulas A and B, R, $R_1$, $R_2$, and $R_3$ may or may not be the same. In one embodiment the acidic ionic liquid catalyst is N-butylpyridinium chloroaluminate.

In one embodiment the ionic liquid comprises a cation selected from the group consisting of an alkyl-pyridinium, an alkyl-imidazolium, or a mixture thereof. In another embodiment the ionic liquid can have the general formula RR'R"NH$^+$ $Al_2Cl_7^-$, wherein N is a nitrogen containing group, and wherein RR' and R" are alkyl groups containing 1 to 12 carbons, and where RR' and R" may or may not be the same.

The presence of the first component can give the ionic liquid a Lewis acidic character. In one embodiment the ionic liquid includes strongly Lewis acidic anions, such as $Al_2Cl_2^-$. $Al_2Cl_7^-$, for example, is a strongly Lewis acidic anion, while $AlCl_4^-$ is not. Generally, the greater the mole ratio of the first component to the second component, the greater is the acidity of the acidic ionic liquid.

In one embodiment, the acidic ionic liquid comprises less than one wt %, less than 0.5 wt %, or no, silyl-containing groups. Silyl-containing groups comprise $H_3Si$— or hydrocarbyl derivatives thereof, e.g. $R_3Si$—. Examples of silyl-containing groups are siloxanes and silanes. Siloxanes, for example, are typically not stable in very strongly acidic media.

The ionic liquid serves as an adsorbent and promoter for the Brønsted acid. An adsorbent is a substance, usually porous, that allows the molecules of a gas or liquid to adhere to its large surface area. A promoter is a substance that will accelerate the effect of a catalyst on a reaction. A Brønsted acid is any substance that can donate an H$^+$ ion to a base. Brønsted acids are H$^+$-ion or proton donors. Examples of Brønsted acids are HCl, HBr, HI, HF, sulfuric acid, +NH$_4$, NH$_3$, CH$_3$CO$_2$H, H—CH$_2$COCH$_3$, H—C≡CH, H—CH$_3$, and mixtures thereof. In one embodiment, the Brønsted acid is selected from the group consisting of HCl, HBr, HI, HF, sulfuric acid, and mixtures thereof. In another embodiment, the Brønsted acid is a gas, such as hydrochloric acid gas.

In one embodiment the porous solid is placed in a fixed bed or a fluidized bed. A fixed bed has a solid support held in a stable position in a reactor. A fluidized bed has solid particles that are at least partially suspended in a reactor such that the solid particles are substantially free to move about within the reactor, as driven by the flow of a feed stream through the reactor. In one aspect, the porous solid is placed in the fixed bed or fluidized bed and the feed stream is introduced at one end of the reactor and withdrawn at the opposite end of the reactor. In one embodiment the end where the feed stream is introduced is the top and the opposite end is the bottom. There can be a grid at the opposite end of the reactor to hold the porous solid inside the reactor, but to allow the fluid products to pass through.

In one embodiment, the chemical reactor additionally comprises a void largely open to hydrocarbon flow. For example, the void can be greater than 2 volume % of the chemical reactor, such as from 10 to 80 volume %, or from 20 to 60 volume %.

An alkylating agent is a chemical that can add alkyl groups (for example, ethyl or methyl groups) to another molecule. Examples of alkylating agents are cyclopropane, alkyl halides, aliphatic alcohols, alkyl ethers, alkyl esters, olefins, and mixtures thereof. In one embodiment the alkylating agent comprises an olefin. The olefin can be a single olefin, or a mixture of olefins. The olefin can be an alpha olefin, an internal olefin, or a combination thereof. In one embodiment the olefin comprises a $C_2$-$C_{12}$ olefin. In another embodiment the olefin comprises $C_2$-$C_{25}$, or $C_{12}$-$C_{25}$ olefins. The olefin can be made by a number of processes known to those skilled in the art, including thermal cracking, catalytic dehydrogenation, catalytic cracking (e.g., fluid catalytic cracking (FCC)), Fischer-Tropsch synthesis, oxidative chlorination of methane, dehydration of alcohols, and oligomerization of ethylene. In one embodiment the alkylating agent comprises mixed butenes, mixed pentenes, or a combination thereof. These alkylating agents can be produced, for example in a FCC unit.

In one embodiment, the alkylating agent comprises at least 15 wt % 1-butene and the one or more liquid hydrocarbons comprise a bright stock. By increasing the amount of alpha olefin, e.g., 1-butene, in the alkylating agent, the wt % bright stock that is produced can be increased. The wt % bright stock, for example, can be adjusted from 0.1 wt % to 20 wt % by adjusting the amount of alpha olefin in the alkylating agent.

The alkylatable hydrocarbon is a hydrocarbon that is capable of having an alkyl group added to or substituted into it. Examples of these hydrocarbons are olefins, isoparaffins, branched naphthenes, aromatic hydrocarbons, and mixtures thereof. In one embodiment the alkylatable hydrocarbon is a $C_4$-$C_{25}$ isoparaffin, for example isobutane or isopentane. In some embodiments the alkylatable hydrocarbon comprises one or more $C_{12}$-$C_{25}$ isoparaffins or olefins. These heavier types of alkylatable hydrocarbons are available from several sources, including from Fischer-Tropsch condensate.

In one embodiment the alkylatable hydrocarbon comprises an isoparaffin and the alkylating agent comprises an olefin. For example, in one embodiment the hydrocarbon stream comprises a $C_4$-$C_{25}$ isoparaffin and a $C_2$-$C_{12}$ olefin.

In another embodiment the at least one alkylatable hydrocarbon and the at least one alkylating agent both comprise olefins. This can be the case, for example, when the one or more liquid hydrocarbon products are oligomer products. Oligomer products are polymers having only a few monomer units such as a dimer, trimer, tetramer, etc., or their mixtures.

In one embodiment the hydrocarbon mixture comprises mixed olefins.

Gasoline blending components can be blended into gasoline or used directly as gasoline. Examples of gasoline blending components are naphtha and heavy naphtha. In the context of this disclosure, naphtha has a boiling range distribution less than 130° C. and heavy naphtha has a boiling range distribution from 130 to 200° C. In one embodiment, the gasoline blending component has a high octane number. Examples of high octane numbers are 82 or higher, 85 or higher, 90 or higher, and 95 or higher. Different methods are used for calculating octane numbers of fuels or fuel blend components. The Research-method octane number (RON) is determined using ASTM D 2699-07a. RON employs the standard Cooperative Fuel Research (CFR) knock-test engine. Additionally, the Research-method octane number can be calculated [RON (GC)] from gas chromatography boiling range distribution data. The RON (GC) calculation is described in the publication, Anderson, P. C., Sharkey, J. M., and Walsh, R. P., "Journal Institute of Petroleum", 58 (560), 83 (1972). Another measure of the octane number of a fuel is the motor octane number (MON). MON correlates with commercial automotive spark-ignition engine antiknock performance under severe conditions of operation. MON can be determined by ASTM D 2700-09.

In one embodiment the one or more liquid hydrocarbons comprise a gasoline blending component, a middle distillate, a lubricant, or a mixture thereof. A "middle distillate" is a hydrocarbon product having a boiling range between 250° F. to 735° F. (121° C. to 391° C.). The term "middle distillate" includes the diesel, heating oil, jet fuel, and kerosene boiling range fractions. It can also include a portion of naphtha or light oil. In the context of this disclosure, a "lubricant" is a hydrocarbon boiling in the range of about 650° F. (343 degree Celsius) and higher. Lubricants can be blended with additives and used for example as diluents for the additives or in finished lubricants.

The test methods used for boiling range distributions of the products in this disclosure are ASTM D 2887-06a and ASTM D 6352-04. The test method is referred to herein as "SIMDIST". The boiling range distribution determination by distillation is simulated by the use of gas chromatography. The boiling range distributions obtained by this test method are essentially equivalent to those obtained by true boiling point (TBP) distillation (see ASTM Test Method D 2892), but are not equivalent to results from low efficiency distillations such as those obtained with ASTM Test Methods D 86 or D 1160.

In one embodiment, a fresh ionic liquid is added continuously to the chemical reactor and a passivated ionic liquid is withdrawn continuously from the chemical reactor. By continuously adding fresh ionic liquid to the chemical reactor the catalyst activity can be controlled. The passivated ionic liquid can be regenerated in full or in part, and recycled back to the reactor. Because the ionic liquid is in the reactor with a solid support, the average residence time for the ionic liquid in the chemical reactor can be different than the average residence time for the isoparaffin and olefin in the chemical reactor. This is different than in earlier reactor designs where the ionic liquid was mixed and agitated with the hydrocarbon mixture, forming an emulsion.

In one embodiment, the ionic liquid and the one or more liquid hydrocarbons made in the chemical reactor do not form an emulsion. One technical advantage of a chemical reactor where an emulsion is not formed is that the phase separation of the ionic liquid from the liquid hydrocarbons can be less difficult, and this is especially helpful in embodiments where lubricants and/or bright stock are being produced. Bright stock is a lubricant having a kinematic viscosity above 180 $mm^2/s$ at 40° C.

In one embodiment, the difference between the average residence time for the hydrocarbon mixture and the average residence time for the ionic liquid in the chemical reactor is at least 30 seconds, at least 1 minute, at least 2 minutes, at least 5 minutes, or at least 8 minutes. The flow of the ionic liquid during a step of introducing the ionic liquid to the chemical reactor and the flow of the at least one isoparaffin and the at least one olefin can be varied independently to optimize the process.

In one embodiment the chemical reactor is operated adiabatically. During an adiabatic process, any temperature changes are due to internal system fluctuations, and there is no externally supplied heating or cooling. Operating in this mode can provide significant equipment savings and reductions in process complexity. One way that temperature in the chemical reactor can be maintained in a suitable range is by having a volatile hydrocarbon from a reaction zone in the chemical reactor evaporate to cool the reactor. By having a volatile hydrocarbon from an alkylation reaction zone evaporate to cool the chemical reactor the temperature in the reactor can be maintained within 10° C., within 5° C., or within 1° C. In one embodiment, a volatile hydrocarbon from the reaction zone in the chemical reactor evaporates to cool the chemical reactor and the chemical reactor is maintained at a temperature from 25 to 60° C., such as 30 to 50° C., 35 to 45° C., or 35 to 40° C. This means of cooling the chemical reactor is highly scalable, and can be used on any chemical reactor size from a small micro-unit chemical reactor in a research lab, to an chemical reactor in a pilot plant, and up to a full size chemical reactor in a large refinery operation. Examples of volatile hydrocarbons from the reaction zone that can provide cooling include $C_6^-$ normal alkanes, isoparaffins, and olefins. Specific examples are ethylene, ethane, propane, n-butane, isobutane, isobutene, and mixtures thereof.

In one embodiment, the chemical reactor comprises:
a) gaseous HCl, which is a catalyst for oligomerization of olefins;
b) a chloroaluminate ionic liquid, supported on a porous solid, wherein the
  chloroaluminate ionic liquid serves as an adsorbent and promoter for the catalyst; and
c) a volatile hydrocarbon, which evaporates to control a heat of reaction in the chemical reactor. In this embodiment, for example, the olefins can comprise propene and the volatile hydrocarbon can be n-butane.

In other embodiments, cooling can be provided by a heat transfer fluid or coolant. In some embodiments the chemical reactor is cooled by transferring heat through a wall of the chemical reactor.

In one embodiment, greater than 95 wt % of at least one olefin in the hydrocarbon mixture is converted in the chemical reactor. In other embodiments, the wt % of the olefin that is converted is greater than 97 wt %, greater than 98 wt %, greater than 99 wt %, or 100 wt %. High levels of conversion are desired so to most efficiently use the olefin and to not require recapturing it or recycling it from the effluent.

In one embodiment, the feed rate of at least one olefin in the hydrocarbon mixture to the chemical reactor is higher than is what is typically used in either continuously stirred tank reactors or nozzle loop reactors. For example, the feed rate of the olefin can be at least 1.2 LHSV, at least two LHSV, at least three LHSV, up to as high as 50 LHSV. This high feed rate means that the volume of the chemical reactor to convert a given amount of olefin is reduced. The reduction in the chemical reactor volume can be inversely proportional to the feed rate. LHSV is the linear hourly space velocity, defined as the ratio of the hourly volume of oil processed to the volume of catalyst. It is generally expressed as v/v/hr or $hr^{-1}$.

The quality of the one or more liquid hydrocarbons produced by the process can be exceptional. For example the one or more liquid hydrocarbons that are heavy naphtha or jet fuel can have a high smoke point, such as a smoke point of 30 mm or higher, 35 mm or higher, or 40 mm or higher. Smoke point can be determined by ASTM D 1322-08. In the context of this disclosure, heavy naphtha has a boiling range from 130-200° C., and jet fuel has a boiling range from 200-290° C. In another example, the one or more liquid hydrocarbons comprise a bright stock. The bright stock can have a high viscosity index (VI), such as 75 or higher, 80 or higher, 90 or higher, 100 or higher, 110 or higher, or 120 or higher. In one embodiment the one or more liquid hydrocarbons comprise a bright stock having a kinematic viscosity at 100° C. of 200 $mm^2/s$ or higher and a VI of 80 or higher. VI is determined by ASTM D 2270-04.

In one embodiment, the one or more liquid hydrocarbons in the effluent from the chemical reactor comprise at least 2 wt % hydrocarbons with a boiling point greater than 500° C. In other embodiments the one or more liquid hydrocarbons in the effluent from the chemical reactor comprise at least 3 wt %, at least 4 wt %, at least 5 wt %, at least 6 wt %, or at least 8 wt % hydrocarbons with a boiling point greater than 500° C. In one embodiment, the hydrocarbons with a boiling point greater than 500° C. are 60 wt % or less.

In one embodiment, the one or more liquid hydrocarbons comprise: a) at least 5 wt % hydrocarbons with a boiling point less than 130° C. and having a RON of 90 or higher, and b) at least 2 wt % hydrocarbons with a boiling point greater than 500° C. and a VI of 100 or higher. In another embodiment, the one or more liquid hydrocarbons comprise: a) at least 5 wt % hydrocarbons with a boiling point less than 130° C. and having a RON of 90 or higher, and b) a bright stock with a VI greater than 100. In yet another embodiment, the one or more liquid hydrocarbons comprise: a) a lubricant having a kinematic viscosity of 180 mm$^2$/s or less at 40° C. and a VI greater than 15, and b) a bright stock with a VI greater than 100.

EXAMPLES

Example 1

A reactor was dense-packed with a fixed bed of silica gel (4.0 g/9.5 ml DAVISIL™ silica gel, Type 60 Å, 35-60 mesh, 250-500 μm particle size). DAVISIL® is a registered trademark of W.R. Grace & Co. Prior to packing the reactor, the silica gel was dried in a stream of nitrogen at 200° C. The reactor was a 50 cm ¼" ID perfluoroalkoxy (PFA) tube. Small patches of glass wool were applied at each end of the PFA reactor tube to keep the silica gel in place. The volume of the fixed bed in the PFA reactor tube was about 15 ml. This reactor was part of a laboratory process unit, which is illustrated in FIG. 1.

Three feed streams were fed to the PFA reactor tube. The tests done using the PFA reactor tube were all done at ambient pressure and at ambient inlet temperature. The first feed stream was gaseous HCL, which was pumped to the PFA reactor tube using an FMI piston pump operated with an inlet pressure of about 2-3 psi above ambient. The second feed stream was a hydrocarbon feed comprising 2-pentene and isopentane as reactants. The second feed stream was pumped to the PFA reactor tube using another FMI piston pump. The third feed stream was N-butylpyridinium chloroaluminate ($C_5H_5C_4H_9Al_2Cl_7$) ionic liquid catalyst. The third feed stream was pumped to the PFA reactor tube using a peristaltic pump.

Before introduction of the 2-pentene in the second feed stream into the PFA reactor tube, the PFA reactor tube was filled with isopentane flowing at a rate of 5 ml/min. Subsequently, the ionic liquid catalyst was slowly added to the isopentane flowing into the PFA reactor tube until about half of the PFA reactor tube volume was loaded with ionic liquid catalyst. The loading of the ionic liquid catalyst was visible from the outside of the PFA reactor tube because the silica gel turned yellow brown as it became loaded with the ionic liquid catalyst.

Once visual inspection showed that half of the PFA reactor tube was loaded with ionic liquid catalyst, flow of ionic liquid catalyst was stopped while isopentane flow was continued for an additional 4 minutes to allow the ionic liquid catalyst to settle into the silica gel support. It is believed that when the PFA reactor tube was loaded that the ionic liquid catalyst filled the pore volume of the silica gel, wetted the surface of the particles, and left a void largely open to hydrocarbon flow. The volume of ionic liquid catalyst in the PFA reactor tube was estimated to be 4 ml.

After the ionic liquid catalyst had settled into the silica gel support, the hydrocarbon feed was changed to 5 ml/min 2% 2-pentene in isopentane (approximately 0.90 mmole olefin/min) HCl was also added to the PFA reactor tube at a flow of about 1 Nml/min (0.04 mmole/min).

Liquid GC samples of hydrocarbons were collected from the PFA reactor tube effluent. The samples of hydrocarbons were each washed with water immediately after collection. The liquid GC samples were taken every 5 minutes for the first 20 minutes after the hydrocarbon feed was changed. All these samples showed 100% olefin conversion, yielding an liquid hydrocarbon rich in iso-$C_{10}$ boiling range material.

After the first 20 minutes, the HCl flow was stopped and sampling of hydrocarbons continued to be taken every 5 minutes for the next 30 minutes. Again, all the samples showed 100% olefin conversion. The hydrocarbon feed was changed a second time to 5 ml/min 5 wt % 2-pentene in isopentane (approximately 2.2 mmoles olefin/min). A liquid GC sample of hydrocarbons collected from the PFA reactor tube effluent 8 minutes after the hydrocarbon feed was changed a second time showed 100% olefin conversion. A liquid GC sample of hydrocarbons collected from the PFA reactor tube effluent 15 minutes after the hydrocarbon feed was changed a second time showed 99.7% olefin conversion. A liquid GC sample of hydrocarbons collected from the PFA reactor tube effluent 20 minutes after the hydrocarbon feed was changed a second time showed only 72% olefin conversion.

When the liquid GC sample of hydrocarbons collected from the PFA reactor tube showed only 72% olefin conversion the HCl flow was started again at a flow of about 1 Nml/min. 10 minutes after the restarting of the HCl the liquid GC sample of hydrocarbons collected from the PFA reactor tube effluent showed 99.9% olefin conversion.

While feeding the 5 wt % 2-pentene a substantial part of the isopentane evaporated, causing a gas flow out of the PFA reactor tube. This gas flow was caused by the heat of reaction in the PFA reactor tube. The gas flow was countered by submerging the PFA reactor tube in cold water.

Example 2

Figure 2:
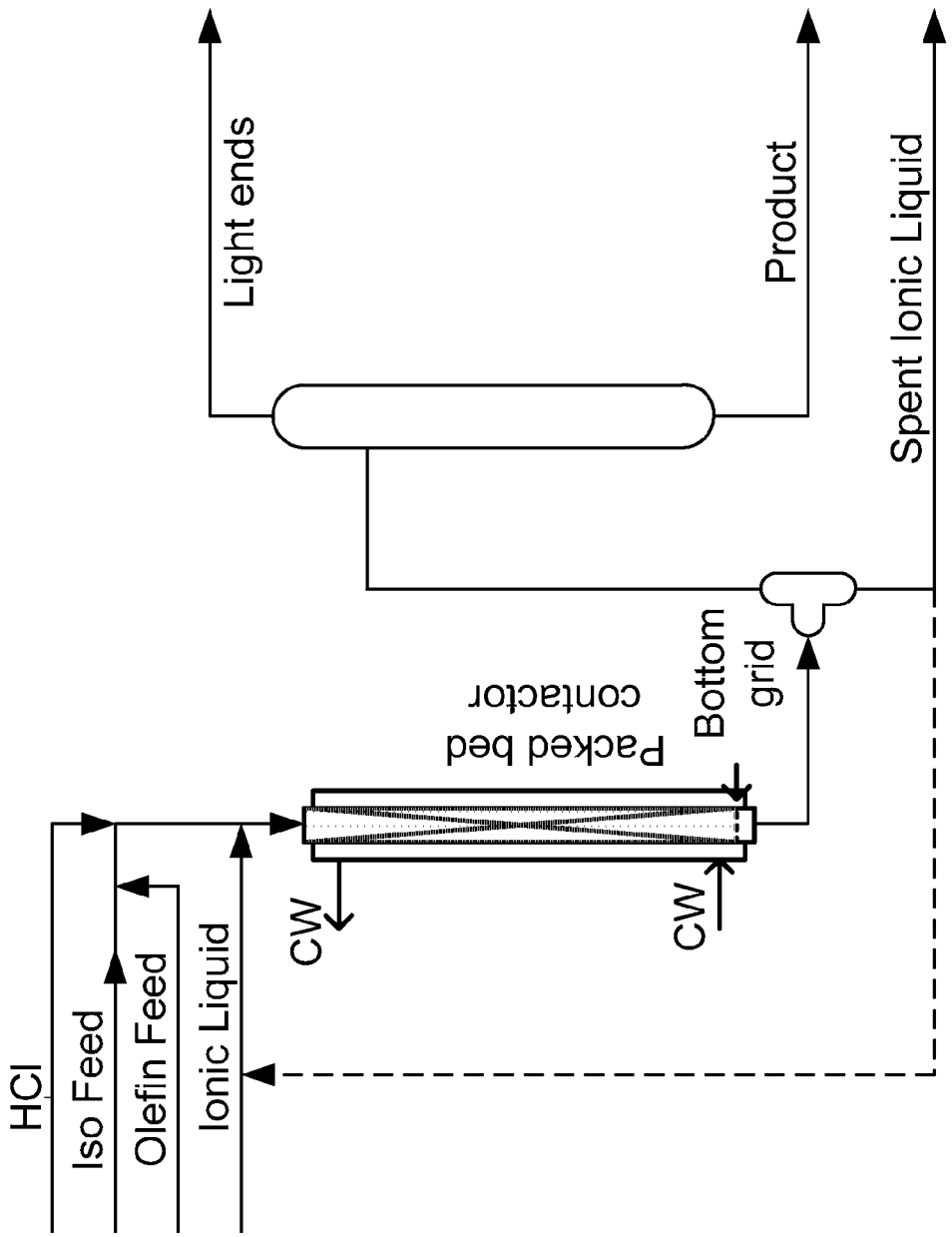
FIG. 2 is a process flow diagram of the experimental setup used for Example 2 in this disclosure.

4.0 g/9.5 ml DAVISIL™ Type 60 Å, 35-60 mesh, silica gel was dried in a stream of nitrogen at 180° C. The dried silica gel was loaded into an 8" long, ⅜" OD reactor tube (packed bed contactor) with a cooling mantle for cooling brine. Once loaded into the reactor tube, the silica gel had a volume of roughly 1 ml/g. This packed bed contactor was part of a laboratory process unit, which is illustrated in FIG. 2.

A series of five experiments were conducted, where a combined feed stream comprising pure isoparaffin (Iso Feed) and different olefin feeds were fed to the packed bed contactor. The olefin feeds were passed through a mol sieve drier, but had no further purification, diene saturation or isomerization prior to being fed to the packed bed contactor. The combined feed stream was mixed with a small amount of HCl and fed to the top of the packed fed contactor along with a flow of ionic liquid. The ionic liquid was N-butylpyridinium chloroaluminate ($C_5H_5C_4H_9Al_2Cl_7$) ionic liquid catalyst. The volume distributions in the packed bed contactor were estimated to be about 40 vol % pore volume (most of which was filled by ionic liquid during operation), about 40 vol % void (part of which was filled by ionic liquid during operation), and 20 vol % $SiO_2$ framework.

The different olefin feeds that were tested included mixed FCC butenes and mixed FCC pentenes. The mixed FCC butenes were combined with isobutane and the mixed FCC pentenes were combined with isopentane. The mixed FCC butenes comprised approximately 20 wt % 1-butene.

An effluent was collected at the bottom of the packed bed contactor during each run. The effluent was depressurized, the ionic liquid phase separated out, and the hydrocarbons fractionated into a $C_4^-$ vent gas and a $C_5^+$ liquid product. Each liquid product sample was analyzed by SIMDIS and the chloride content determined by XRF. Groups of samples made under similar conditions were combined and distilled into six fractions with different boiling point ranges. These were: naphtha (<130° C./<275° F.), heavy naphtha (130-200° C./275-390° F.), jet fuel (200-290° C./390-550° F.), diesel (290-360° C./550-680° F.), neutral base oil (360-500° C./680-930° F.), and bright stock (>500° C./>930° F.). Each fraction was subsequently analyzed, and selected data is summarized in Table I.

TABLE I

| | Run 1 | Run 2 | Run 3 | Run 4 | Run 5 |
|---|---|---|---|---|---|
| Reaction Temperature, ° C. | 10-20 | 10-20 | 10-20 | Adiabatic, 40 | Adiabatic, 35 |
| Olefin Feed | FCC Butenes | FCC Butenes | FCC Butenes | FCC Butenes | FCC Pentenes |
| Iso Feed | Isobutane | Isobutane | Isobutane | Isobutane | Isopentane |
| I/O | 3.5-9 | 2.8-4.2 | 8 | 7.6 | 3.7-4.7 |
| Olefin/HCl, mole/mole | 250-640 | 260-730 | 60 | 60 | 77 |
| Olefin/IL, g/g | 0.3-1.3 | 4.5-26 | 4.3-4.5 | 2.5-5 | 7 |
| Olefin LHSV | 3-7 | 6-19 | 6.1 | 6.6 | 9 |
| Olefin Conversion, wt % | >98 | 60-94 | 99-100 | 99-100 | 100 |
| Wt % Naphtha | 14.5 | 12.0 | 21.4 | 25.8 | 20.5 |
| RON | | | 97.00 | 94.4 | |
| MON | | | 92.00 | | |
| Wt % Heavy Naphtha | 9.5 | 5.7 | 11.3 | 11.5 | 29.9 |
| Bromine Number | 48 | 59 | 12 | 21 | 106 |
| Density, 60° F., g/ml | 0.75 | 0.77 | 0.75 | 0.75 | 0.77 |
| API at 60° F. | 56.0 | 53.0 | 56.6 | 56.2 | 52.9 |
| RON | | 95.9 | | | |
| Smoke Point, mm | 37.00 | 37.00 | 43.00 | 42.00 | 30.00 |
| Flash Point, ° C. | | | 25.00 | 40.00 | 34.00 |
| Cloud Point, ° C. | <-60 | <-60 | <-60 | <-60 | <-60 |
| Freeze Point, ° C. | <-60 | <-60 | <-60 | <-60 | <-60 |
| Viscosity, @-20° C., mm²/s | 2.89 | 2.98 | 3.34 | 3.38 | 2.40 |
| Wt % Jet Fuel | 18.6 | 19.9 | 19.0 | 17.5 | 29.7 |
| Bromine Number | 64 | 70 | 37 | 43 | 82 |
| Density, 60° F., g/ml | 0.80 | 0.80 | 0.79 | 0.80 | 0.81 |
| API at 60° F. | 45.3 | 44.8 | 47.1 | 45.4 | 44.2 |
| Smoke Point, mm | 30.00 | 31.00 | 34.00 | 35.00 | 26.00 |
| Flash Point, ° C. | 97.00 | 87.00 | 93.00 | 87.00 | 88.00 |
| Cloud Point, ° C. | <-60 | <-60 | | <-60 | <-60 |
| Freeze Point, ° C. | <-60 | <-60 | | <-60 | <-60 |
| Viscosity, @-20° C., cP | 29.13 | 21.68 | 25.26 | 17.66 | 19.92 |
| Wt % Diesel | 20.2 | 23.1 | 17.8 | 22.3 | 12.9 |
| Bromine Number | 43 | 58 | 50 | 52 | 71 |
| Density, 60° F., g/ml | 0.82 | 0.82 | 0.82 | 0.82 | 0.83 |
| API at 60° F. | 40.1 | 41.1 | 41.0 | 41.9 | 38.5 |
| Cetane Number | | 25.60 | 25.30 | | |
| Kinematic Viscosity at 40° C., mm²/s | 15.04 | 12.58 | 13.2 | 10.81 | 13.86 |
| Wt % Neutral Base Oil | 30.6 | 37.2 | 29.7 | 20.6 | 5.6 |
| Bromine Number | 38 | 30 | 36 | 38 | 50 |
| Density, 60° F., g/ml | 0.85 | 0.85 | 0.84 | 0.84 | 0.86 |
| API at 60° F. | 34.4 | 35.7 | 0.84 | 0.84 | 0.86 |
| Kinematic Viscosity at 40° C., mm²/s | 124.8 | 155.4 | 164.6 | 120.8 | |
| Kinematic Viscosity at 100° C., mm2/s | 10.1 | 10.8 | 10.8 | 9.1 | |
| VI | 39 | 17 | 4 | 11 | |
| Pour Point, ° C. | -27 | -25 | -21 | -25 | |
| Wt % Bright Stock | 6.6 | 2.1 | 0.8 | 2.2 | 0 |
| Bromine Number | 4 | 9 | | | |
| Density, 60° F., g/ml | 0.92 | 0.91 | 0.98 | | |
| API at 60° F. | 23.0 | 24.8 | 12.4 | | |
| Kinematic Viscosity at 40° C., mm²/s | 19015 | 17195 | | | |
| Kinematic Viscosity at 100° C., mm²/s | 486 | 352 | | | |
| VI | 153 | 122 | | | |
| Pour Point, ° C. | 4 | 6 | | | |

During runs 1-3 the reaction temperature was controlled by cooling the packed bed contactor with a recirculation cooling medium.

During runs 4 and 5 the packed bed contactor was operated without external cooling, i.e. adiabatically. The packed bed contactor was kept cool by using in-situ evaporation of light components in the effluent. It is notable that even with the removal of light components in the effluent that greater than 98 wt % olefin conversion was achieved.

During the runs with mixed FCC butenes the fixed bed contactor was maintained at 50 psi. Ionic liquid was recycled from the effluent back to the fixed bed contactor at a rate of 0.5 to 1 g/min (0.4 to 0.8 ml/min) with a small make up of fresh ionic liquid (less than 10 wt %). The fresh ionic liquid was added to maintain a fairly constant level of conjunct polymer in the ionic liquid. The feed stream comprising the mixed FCC butenes was flowed to the fixed bed contactor at 5.5 to 6 ml/min. The average residence time for the FCC butenes in the fixed bed contactor was about 30 min. and the average residence time for the ionic liquid in the fixed bed contactor as between about 5 and 10 min. The volumetric ratio of ionic liquid to FCC butenes was about 1:1. One advantage of using the fixed bed contactor was that there was a difference between the average residence times for the hydrocarbon feed and the ionic liquid in the reactor. Thus the feed flows can be varied independently, given an added process optimization handle.

The olefin space velocities during the five different runs varied from 3 to 19 LHSV. These space velocities were much higher, approximately 10 times higher, than what would be needed using a continuously stirred tank reactor. This means that the reactor volume for converting a given olefin stream was considerably smaller, e.g. greater than 5 or 10 times smaller than what would be needed in a CSTR for an equivalent olefin conversion of a given olefin stream.

It is notable that the smoke points of the heavy naphtha and jet products produced in the runs with FCC mixed butenes were high, generally 30 mm or higher.

It is also notable that the bright stocks produced in the fixed bed contactor had VIs that met the requirements for API Group III base oil. They had high kinematic viscosities, 200 mm$^2$/s or higher at 100° C., and VIs of 120 or higher. The yields of bright stock were at least 2 wt % of the total products made in the fixed bed contactor in three of the runs using mixed FCC butenes.

In Run 1 and Run 2 significant amounts of both a lubricant and a bright stock were produced. An unusual feature in these runs was that the difference in the VIs of the lubricant and the bright stock made in a single run was high, for example at least 50, at least 75, at least 85, or at least 100. The conditions during these runs favored the formation of heavy oligomers having desired low levels of branching and favorable placement of the branches in the molecules.

The molar ratio of the at least one olefin to the Brønsted acid was 250 or greater in both Run 1 and Run 2. The high molar ratios of the at least one olefin to the Brønsted acid in these two runs provided selectivity towards producing at least 31 wt % products from the chemical reactor that boiled at 360° C. or higher. When the chemical reactor was operated with high molar ratios of the at least one olefin to the Brønsted acid, oligomerization also occurred in the chemical reactor. Oligomerization is a chemical process that converts monomers to a finite degree of polymerization. Dimers, trimers and tetramers are examples of oligomers formed by oligomerization. In one embodiment the oligomerization is olefin oligomerization.

In contrast, the molar ratio of the at least one olefin to the Brønsted acid was less than 100 in Runs 3, 4, and 5. The lower molar ratios of the at least one olefin to the Brønsted acid provided selectivity towards producing lighter products, and less than 31 wt % of the products from the alkylation reactor boiled at 360° C. or higher in these three runs. By adjusting the molar ratio of the at least one olefin to the Brønsted acid, the alkylation reactor could operate in different modes with varying product selectivity.

The term "comprising" means including the elements or steps that are identified following that term, but any such elements or steps are not exhaustive, and an embodiment can include other elements or steps. For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof

The invention claimed is:

1. A chemical reactor, comprising:
   a) an ionic liquid, supported on a porous solid in a fixed bed for an average residence time that is longer than the average residence time of hydrocarbons in the reactor; wherein the porous solid comprises a particulate having a diameter in the longest direction from 250 to 3000 µm; and
   b) a Brønsted acid; wherein the ionic liquid serves as an adsorbent and promoter for the Brønsted acid, and the Brønsted acid is a catalyst for alkylation, oligomerization, or a combination thereof of a hydrocarbon mixture comprising at least one alkylatable hydrocarbon and at least one alkylating agent in the chemical reactor.

2. The chemical reactor of claim 1, wherein the Brønsted acid is selected from the group consisting of HCl, HBr, HI, HF, sulfuric acid, and mixtures thereof.

3. The chemical reactor of claim 1, wherein the Brønsted acid comprises hydrochloric acid gas.

4. The chemical reactor of claim 1, wherein the ionic liquid has a general formula RR' R" N H$^+$Al$_2$Cl$_7^-$, wherein N is a nitrogen containing group, and wherein RR' and R" are alkyl groups containing 1 to 12 carbons, and where RR' and R" may or may not be the same.

5. The chemical reactor of claim 1, wherein the ionic liquid comprises a cation selected from the group consisting of an alkyl-pyridinium, an alkyl-imidazolium, or a mixture thereof.

6. The chemical reactor of claim 1, wherein the ionic liquid comprises less than one wt % silyl-containing groups.

7. The chemical reactor of claim 1, wherein the diameter in the longest direction is from 250 to 500 µm.

8. The chemical reactor of claim 1, wherein the porous solid is selected from the group consisting of silica, alumina, titania, zirconia, thoria, boria, and mixtures thereof.

9. The chemical reactor of claim 1, wherein the porous solid has pores in the range of 20 to 150 Å.

10. The chemical reactor of claim 1, additionally comprising a void largely open to hydrocarbon flow that is from 10 to 80 volume % of the chemical reactor.

11. The chemical reactor of claim 1, wherein a pore volume in the reactor is greater than 25 vol % of a total volume of the reactor.

12. The chemical reactor of claim 1, wherein the ionic liquid comprises a strongly Lewis acidic anion.

13. The chemical reactor of claim 1, additionally comprising a pump to provide the average residence time.

14. The chemical reactor of claim 13, wherein the pump is a peristaltic pump.

15. The chemical reactor of claim 1, additionally comprising a grid, at an end of the chemical reactor opposite from where a feed stream is introduced, that holds the porous solid inside the chemical reactor and allows a passivated ionic liquid to pass through.

16. A chemical reactor, comprising:
   a) a gaseous HCl, which is a catalyst for oligomerization of olefins;
   b) a chloroaluminate ionic liquid, supported on a porous solid in a fixed bed for an average residence time, wherein the chloroaluminate ionic liquid serves as an adsorbent and promoter for the catalyst, wherein the porous solid comprises a particulate having a diameter in the longest direction from 250 to 3000 μm; and
   c) a volatile hydrocarbon, which evaporates to control a heat of reaction in the chemical reactor.

17. The chemical reactor of claim 16, wherein the diameter in the longest direction is from 250 to 500 μm.

18. A chemical reactor, comprising:
   an ionic liquid, supported on a porous solid in a fixed bed or a fluidized bed for an average residence time, wherein a fresh ionic liquid is added to the chemical reactor and a passivated ionic liquid is withdrawn from the chemical reactor;
   b) a Brønsted acid; wherein the ionic liquid serves as an adsorbent and promoter for the Brønsted acid, and the Brønsted acid is a catalyst for alkylation, oligomerization, or a combination thereof of a hydrocarbon mixture comprising at least one alkylatable hydrocarbon and at least one alkylating agent in the chemical reactor;
   c) a grid, at an end of the chemical reactor opposite from where a feed stream is introduced, that holds the porous solid inside the chemical reactor and allows the passivated ionic liquid to pass through.

19. The chemical reactor of claim 18, wherein the porous solid comprises a particulate having a diameter in the longest direction from 250 to 3000 μm.

20. The chemical reactor of claim 19, wherein the diameter in the longest direction is from 250 to 500 μm.

21. The chemical reactor of claim 18, wherein the ionic liquid is supported on the porous solid in the fixed bed.

* * * * *